United States Patent
Hooreman

(12) 
(10) Patent No.: US 6,440,413 B1
(45) Date of Patent: Aug. 27, 2002

(54) MEDICAMENT FOR OPTIMIZING MUCOSAL VISCOSITY AND STIMULATING INTESTINAL FUNCTION

(76) Inventor: Michel Hooreman, 10 rue du Delta, Paris, F-75009 (FR)

( * ) Notice: Subject to any disclaimer, the term of this patent is extended or adjusted under 35 U.S.C. 154(b) by 0 days.

(21) Appl. No.: 09/717,808

(22) Filed: Nov. 20, 2000

Related U.S. Application Data

(63) Continuation-in-part of application No. 09/155,534, filed as application No. PCT/FR97/00614 on Apr. 5, 1996, now abandoned.

(30) Foreign Application Priority Data

Apr. 5, 1996 (FR) .............................. 96 04310

(51) Int. Cl.⁷ ...................... A61K 38/48; C12N 9/58
(52) U.S. Cl. ..................... 424/94.63; 435/223
(58) Field of Search ...... 424/94, 63; 435/223

(56) References Cited

U.S. PATENT DOCUMENTS 5,047,240 A * 9/1991 Hooreman

FOREIGN PATENT DOCUMENTS

GB 1133579 * 11/1968

* cited by examiner

*Primary Examiner*—Jon P. Weber
(74) *Attorney, Agent, or Firm*—Bierman, Muserlian and Lucas

(57) ABSTRACT

The invention pertains to the field of biology, and more particularly, to therapeutic chemistry, and discloses pharmaceutical compositions containing, as an active ingredient, an enzyme or an enzyme complex containing said enzyme, obtained by cultivating *Streptomyces fradiae* under conditions defined in French patent 2.600.340, as a mixture or in combination with a physiologically acceptable, non-toxic and inert carrier or vector. Said pharmaceutical compositions are useful for preventing or treating degenerative diseases, particularly those related to intestinal dysfunction.

9 Claims, No Drawings

MEDICAMENT FOR OPTIMIZING MUCOSAL VISCOSITY AND STIMULATING INTESTINAL FUNCTION

PRIOR APPLICATIONS

This application is a Continuation-in-Part of U.S. patent application Ser. No. 09/155,534 filed Sep. 28, 1998, now abandoned, which is a 371 of PCT/FR97/00614 filed Apr. 5, 1996.

The invention relates to the field of biology, and more particularly to that of therapeutic chemistry.

The invention relates to pharmaceutical and/or dietary compositions based on an enzyme or an enzymatic complex comprising this enzyme, which can contribute towards prevention and/or treatment of diseases.

It more particularly relates to pharmaceutical compositions based on an enzyme or an enzymatic complex comprising this enzyme which stimulate the functions of the intestine and can thus contribute towards prevention and/or treatment of degenerative diseases associated with ageing.

It specifically relates to pharmaceutical compositions comprising, as the active principle, one or more enzymes extracted from or contained in the enzymatic complex obtained by culture of *Streptomyces fradiae* under the conditions defined in French Patent 2,600,340 and in the U.S. Pat. No. 5,047,240 issued Sep. 10, 1991, in the name of the Applicant.

The above-mentioned patent has described the production and use in zootechnology of a new proteolytic complex obtained from a filamentous bacterium, *Streptomyces fradiae*; in the following, this complex is called by its current commercial name: PANSTIMASE®.

This filamentous bacterium can produce simultaneously at least 5 proteinases and 2 peptidases; these 7 enzymes have been described by K. MORIHARA et al. (Biochem. Biophys. Acta, 1967, 139, 382). When they are added together to foods consumed by animals, these 7 enzymes cause an excessive reduction of the viscosity of the intestinal mucus and can then cause ulceration of the intestinal wall. These 7 enzymes thus have adverse effects in zootechnology if they are used together.

Under the conditions indicated in the above-mentioned U.S. patent, PANSTIMASE®, which is made up only of 3 exocellular proteinases, with a preponderance of one of them, and with the exclusion of endocellular proteinases and peptidases, is obtained. When added to foods consumed by animals, PANSTIMASE® causes a moderate reduction in the viscosity of the intestinal mucus, and it is not capable of attacking the intestinal wall.

At the same time as having a relatively moderate action on the proteins of the intestinal mucus, PANSTIMASE® has a more potent action on the proteins of the raw materials used in the composition of foods, which improves their digestibility.

In addition to these direct actions in the intestine, PANSTIMASE® has indirect actions on various organs, in particular on the pancreas; as already indicated in the earlier patent, it has been found that it causes an increase of 50 to 80% in the concentration of enzymes or proenzymes in this organ.

Because of these favourable actions, PANSTIMASE® is now used as a nutritional complement added to foods intended for animals to improve their growth or productivity. It has thus been found that it also improves the resistance of animals to infectious, bacterial or viral diseases, and that it reduces certain adverse effects of ageing.

These findings have suggested the possible use in therapeutics, for both animals and man, of PANSTIMASE® or of the active principles of which it is made up, that is to say the preponderant exocellular proteinase produced by *Streptomyces fradiae* or the mixture of this preponderant exocellular proteinase with at least one of the other two exocellular proteinases produced by *Streptomyces fradiae*.

The active principles of pharmaceutical compositions require additional purification compared with the product used on animals. Under the conditions indicated in the earlier patent, non-purified PANSTIMASE® is obtained, the titre of which is at least equal to 2,000 A.U./mg.

The Anson Unit (abbreviated to A.U.) is defined here as being the amount of enzyme which, when incubated for 10 min at 25° C. and at pH 7.5 in the presence of denatured haemoglobin, liberates from this substrate the equivalent of 1 mcg tyrosine, determined by spectrophotometric absorption at 280 nm on the filtrate which cannot be precipitated by trichloroacetic acid.

Various adjustments to the conditions indicated in the earlier patent allow a semi-purified PANSTIMASE® to be obtained, the titre of which is at least equal to 4,000 A.U./mg. The conventional techniques of fractional precipitation or passage over a column enable each of the 3 proteins of which PANSTIMASE® is composed to be obtained in isolation. The specific activity of the preponderant exocellular proteinase is greater than 100,000 A.U./mg, and is significantly higher than that of the other 2 proteinases; its molecular weight is about 19 kDa and its isoelectric point is about 8.5.

This preponderant proteinase alone explains the main physiological properties of PANSTIMASE®, in particular because of the fact that it alone has a characteristic action on two important proteins: cholera toxin and collagen.

Cholera toxin is the homologue of LT toxin produced by some pathogenic colibacilli; it is composed of the sub-unit A, which is aggressive, and the sub-unit B, which is immunostimulating. At a low concentration comparable to that which exists in the intestine of animals receiving food supplemented with PANSTIMASE®, the preponderant proteinase selectively destroys the sub-unit A without destroying the sub-unit B, which therefore keeps its capacity to stimulate the immune system.

Collagen is the most abundant protein in the animal kingdom: in mammals, the various types of collagen represent about one third of the total proteins. It is known that the solubility of muscular collagen in hot water is high if it originates from young animals and low if it originates from elderly animals.

When the collagen of elderly animals is treated with the preponderant proteinase, its solubility in hot water increases and becomes comparable to that for young animals. It can be concluded that this proteinase causes a certain "rejuvenation" of collagen. The majority of results on animals correspond to tests carried out with non-purified or semi-purified PANSTIMASE®. For man, it could be possible to use either semi-purified PANSTIMASE® or the purified proteinase or proteinases of which it is composed, that is to say the preponderant exocellular proteinase or the mixture of this preponderant exocellular proteinase with at least one of the other two exocellular proteinases, or with a proteinase or proteinases of which the amino acid sequences have at least 60% homology with those of the preponderant exocellular proteinase or with those of the mixture of proteinases as defined above.

The present invention relates to pharmaceutical and/or dietary compositions comprising, as the active principle, the preponderant exocellular proteinase produced by culture of *Streptomyces fradiae*, which has a specific activity greater than 100,000 A.U/mg, a molecular weight around 19 kDa, and an isoelectric point around 8.5, and is capable of selectivity destroying the sub-unit A of cholera toxin without destroying the sub-unit B, as a mixture or in combination with an inert, nontoxic, physiologically acceptable excipient or vehicle.

The present invention also relates to pharmaceutical and/or dietary compositions comprising, as the active principle, the preponderant exocellular proteinase as defined, or the mixture of this preponderant exocellular proteinase with at least one of the other two exocellular proteinases produced by culture of *Streptomyces fradiae*, or a proteinase or proteinases of which the amino acid sequences have at least 60% homology with those of the preponderant exocellular proteinase or with those of the mixture of proteinases as defined above, as a mixture or in combination with an inert, non-toxic, physiological acceptable excipient or vehicle. The homologous proteinases can be extracts of the culture of various microorganisms, and in particular *Streptomyces fradiae* or *Streptomyces griseus.*

The active principle is administered by the oral, pulmonary or genital route in doses of between 5,000 and 100,000 A.U. For this purpose, the active principle, as a mixture or in combination with conventional excipients, if brought into one of the pharmaceutical form suitable for these types of administration.

The active principle is present in particular in one of the customary forms in pharmacotechnology, such as tablets, coated tablets, gelatine capsules, capsules, powders, solutions or suspensions, dry aerosols, ovules and vaginal tablets.

The administration will be one to three times daily, depending on the therapeutic requirement.

The results obtained on animals all seem to have the same origin: the fundamental action of PANSTIMASE® on the intestine; this action has various aspects which will be described successively.

PHARMACOLOGICAL STUDY OF PHARMACEUTICAL COMPOSITIONS ACCORDING TO THE INVENTION ACTION OF PANSTIMASE IN THE INTESTINE

1—Villi

In relatively young rats (about 2 months), examinations under a photon microscope show that the villi have a normal development, both in the control rats and in the treated rats.

In relatively elderly rats (about 7 months), these examinations show that the villi of the control rats are atrophied, while those of rats treated since their weaning at 4 weeks are just as developed as those of rats aged 2 months. It is thus found that PANSTIMASE® causes a certain "rejuvenation" of the intestine, the villi of which keep their initial capacity for development and rapid regeneration for longer.

The intestine is not only a physiologically inactive filter; it is also the largest of the endocrine glands (B. LEBLANC et al. Rec. Med. Vet. 1981, 157 629 K. UVNAS-MOBERG, for SCIENCE, September 1989, 24). Made up of small cells which regenerate rapidly throughout its entire life, the intestine is the organ richest in nucleic acids: DNA+RNA (G. DURAND et al. Ann Biol. Anim. Bioch. Biophys. 1966, 6, 389); it therefore has the highest latent capacity for protein synthesis.

Examination of histology sections of the intestine indicates that PANSTIMASE® allows better expression of this latent capacity, and consequently greater production of several physiologically active compounds: digestive enzymes, hormones (acting on the pancreas, the liver, the brain), immunoglobulins, cytokines, neurotransmitters (for example VIP=vasoactive intestinal peptide), cell growth (or survival) factors . . . This thus explains why PANSTIMASE®, which acts directly in the intestine, can act indirectly on organs and physiological symptoms influenced by the above compounds; it would thus explain, in particular, its remarkable action on the pancreas (A. ESTIVAL et al. Communication at the Metabolism Conference of Nancy, Jan. 25–26, 1979—University of Nancy I).

The intestine is also the organ richest in immune cells, which circulate in blood vessels and lymph vessels, or which collect and multiply in PEYER's patches. These immune cells are a component of MALT (mucosae associated lymphoid tissue), which is subdivided into GALT situated in the intestine and into BALT situated in the bronchi, and which has analogies with SALT situated in the skin. GALT and BALT are interdependent and act in synergism to ensure the immune defence of the mucosa and to contribute towards the defence of the organism as a whole.

Examination of histology sections of the intestine shows that PANSTIMASE® directly stimulates GALT; it can thus indirectly stimulate a general immune defence. This would thus explain the fact that PANSTIMASE® increase the resistance of animals to infectious diseases.

2—Microvilli

In rats, young or elderly, examinations under an electron microscope show that the microvilli in control rats are coated by hyperviscous mucus and by traces of food residues; on the other hand, those of rats treated with PANSTIMASE® appear cleaner, higher and more numerous. PANSTIMASE® can thus increase the total developed surface of microvilli, that is to say their capacity for absorption.

"In vitro", by treating fragments of intestine taken from control rats with PANSTIMASE®, it was found that, without damaging the microvilli, it was possible to eliminate the hyperviscous mucus coating them; this moderate detergent action can take place within a few minutes.

"In vivo", this cleaning of the intestinal mucosa enables closer contact between infectious germs and this mucosa to be established, which can induce multiplication in the intestine of immune cells capable of combating these germs.

3—Secretory Cells and Exocrine Microglands

Various secretory cells (producers of mucus, lysozyme, . . . ) and numerous exocrine microglands are distributed throughout the intestine, into which they discharge significant amounts of secretions (about 2,000 ml per day in man). The flow of these secretions may be restrained or even blocked by the presence of microplugs of mucus.

Examination of histology sections of the intestine shows that PANSTIMASE® deaggregates these microplugs, re-establishes normal flow of these secretions, and causes a reactive increase in their production.

It is known that saliva secretion comprises a cell growth factor: epithelial growth factor (EGF); furthermore, intestinal secretions may comprise growth factors which are capable of acting on enterocytes, lymphocytes . . . The increase in the production of such factors under the action of PANSTIMASE® may explain the better development of villi and GALT found on the histology sections of the intestine of treated rats.

4—PEYER'S Patches

PEYER's patches, which are aggregates of immune cells distributed throughout the intestine, are more numerous in treated rats: they appear from the duodenum in these rats, but only from the jejunum in control rats; they are also more dense: their lymphocytes are smaller, more compact, and seem more active (they are more intensely coloured by the reagents used in histology).

5—Prolonged Non-adhesion of Infectious Germs PANSTIMASE® can counteract prolonged adhesion of infectious germs to the mucosa, and in particular to the intestinal mucosa.

This prolonged adhesion results from the formation of chemical bonds between the adhesins attached to these germs and their receptors attached to the mucosa: adhesins and receptors are complex (glyco-lipo)proteins.

"In vitro" tests have shown that PANSTIMASE®, which has a certain affinity for complex proteins, can cut adhesins or detach the receptors from the mucosa on which they are attached; a rupture in the adhesion often results, which can take place within some tens of minutes.

In addition, PANSTIMASE® can stimulate regeneration of the villi of the intestine, that is to say elimination of old cells which are abnormal or affected by adhesion of infectious germs; this elimination is facilitated by the intensification in the flow of intestinal secretions, production of which is increased under the action of PANSTIMASE®.

It can be seen that although PANSTIMASE® can first allow closer contact between infectious germs and the intestinal mucosa (and induce multiplication in the intestine of immune cells which are capable of combating these germs), it can also then counteract the prolonged adhesion of these germs to the mucosa and their penetration into the underlying tissue.

6—Destruction of Protein Enterotoxins

At concentrations of between 10 and 100 A.U./ml, and by heating at 37° C. for some tens of minutes, PANSTIMASE® destroys several protein toxins, and can thus contribute towards prevention and/or treatment of diarrhoeas. Among the toxins destroyed by PANSTIMASE® there may mentioned botulinus toxin, cholera toxin, the LT toxin produced by pathogenic colibacilli, necrotizing cytotoxic factor also produced by these colibacilli . . .

Under the same conditions, endogenous proteinases (trypsin, chymotrypsin . . . ) do not destroy these toxins and therefore cannot contribute towards prevention and/or treatment of these diarrhoeas.

In the case of LT toxin, PANSTIMASE® destroys the sub-unit A, which is aggressive, without destroying the sub-unit B, which is immunostmulating.

7—Conclusion

PANSTIMASE® has a fundamental action throughout the intestine which stimulates global functioning of this key organ and consequently of all the organism; hence the wide diversity of examples of therapeutic uses.

THERAPEUTIC USES OF PHARMACEUTICAL COMPOSITIONS ACCORDING TO THE INVENTION

The fundamental action of PANSTIMASE® on the intestine enables its use or the use of the active principles of which it is composed, that is to say the preponderant exocellular proteinase or the mixture of this preponderant exocellular proteinase with at least one of the other two exocellular proteinases, to contribute towards prevention or treatment of diseases to be envisaged.

1—Cystic Fibrosis and Respiratory Diseases

Cystic fibrosis is characterized by excessive secretion of too viscous a mucus in the intestinal region and in the bronchial region. All the mucus has the same type of biochemical structure; consequently, PANSTIMASE® can optimize the viscosity of intestinal mucus, bronchial mucus or genital mucus.

The exocellular proteinase or proteinases according to the invention, or the proteinase or proteinases of which the amino acid sequences have at least 60% homology with those of the exocellular proteinase or proteinases of the invention, can be used for the preparation of the medicament intended for optimizing the viscosity of intestinal, bronchial and/or genital mucus.

The exocellular proteinase or proteinases according to the invention, or the proteinase or proteinases of which the amino acid sequences have at least 60% homology with those of the exocellular proteinase or proteinases of the invention, can be used for the preparation of a medicament intended for treatment of cystic fibrosis and disease related to an over-secretion of an intestinal, bronchial and/or genital mucus, and in particular if this is too viscous.

2—Improvement in Absorption and the Blood Circulation

By its moderate detergent action on the intestinal wall, PANSTIMASE® contributes towards improving absorption.

This improvement in absorption can be confirmed by analysing medicaments administered by the oral route in the blood of animals. For example, 50 mg tetracycline without PANSTIMASE® (control group) or in combination with 3 mg PANSTIMASE® having a titre of 400 A.U./mg (treated group) were administered to chickens via a gastric tube; 2.5 ml blood were sampled 2 hours after this administration and it was found that the mean concentration of tetracycline in the serum is 1.35 mcg/ml for the control group and 1.90 mcg/ml for the treated group.

This improvement in the absorption can be analysed more precisely by studying the fixing of medicaments in various organs. For example, a medicamentous food comprising 4 g/kg oxytetracycline without a PANSTIMASE® supplement (control group) or supplemented with 300 mg/kg PANSTIMASE® having a titre of 400 A.U./mg (treated group) was given to trout for 2 days. These fish were then sacrificed and the antibiotic was analysed in the liver, the muscles and the kidneys. It was found that PANSTIMASE® enables a significant increase in the tissue concentration of antibiotic to be obtained, this varying widely according to the organ in question:

+100% in the liver, i.e. 5.75 mcg/g for the treated group v. 2.5 mcg/g for the control group +400% in the muscles, i.e. 1.75 mcg/g for the treated group v. 0.3 mcg/g for the control group +1,000% in the kidneys, i.e. 5.75 mcg/g for the treated group v. 0.5 mcg/g for the control group It seems that PANSTIMASE® causes a better absorption of oxytetracycline and a better distribution of this antibiotic in all the organism, which seems to imply an improvement in blood circulation.

The exocellular proteinase or proteinases according to the invention, or the proteinase or proteinases of which the amino acid sequences have at least 60% homology with those of the exocellular proteinase or proteinases of the invention, can be used for the preparation of a medicament intended for treatment of malabsorption of medicaments or nutrients, and for treatment of disorders in blood circulation; in particular, the medicament is intended for treatment of the wasting found in elderly persons or in patients who have received medicaments which have secondary effects which affect proper functioning of the intestine.

3—Digestive Ulcers and Enterotoxaemias

Digestive ulcers originate from adhesion of a bacterium (*Helicobacter pylori*) to the stomach wall, and some enterotoxaemias originate from adhesion of various infectious germs to the intestinal wall.

PANSTIMASE® counteracts prolonged adhesion of infectious germs to the mucosa and destroys numerous enterotoxins; it can thus contribute towards stimulating the regeneration of the intestine and can prevent and/or treat digestive ulcers and enterotoxaemias.

In fact, in a commercial herd, it was found that PANSTIMASE® is capable of reducing the number of pigs suffering from digestive ulcers, and the mortality due to enterotoxaemias.

The exocellular proteinase or proteinases according to the invention, or the proteinase or proteinases of which the amino acid sequences have at least 60% homology with those of the exocellular proteinase or proteinases of the invention, can be used for the preparation of a medicament intended for prevention and/or treatment of prolonged adhesion of infectious germs to the mucosa, facilitation of the regeneration of atrophied or destroyed villi of the intestinal mucosa, and prevention and/or treatment of digestive ulcers and enterotoxaemias.

4—Diabetes Hepatic Insufficiencies and Disorders in Intestinal Passage

In the earlier patent, it was already indicated that PANSTIMASE® stimulated the exocrine function of the pancreas; in fact, a significant increase in the concentration in the pancreas of all the enzymes or proenzymes analysed has been found: +50% for amylase, +70% for trypsinogen and chymotrypsinogen, +80% for lipase (A. ESTIVAL et al., Communication at the Metabolism Conference of Nancy, Jan. 25–26, 1979 University of Nancy I).

Examination of histology sections of the pancreas then showed that the islets of LANGERHANS are more numerous and have a better appearance in treated rats. These investigations suggest that PANSTIMASE® first stimulates the endocrine function of the pancreas, with consequently a general improvement in protein anabolism, resulting in consecutive stimulation of its exocrine function.

This stimulation exerted on the pancreas is also exerted on the liver, the consequence of which is an improvement in intestinal passage. In an intensive herd, constipation is often observed in confined gestating sows; it has been found that supplementing their food with PANSTIMASE® enables these detrimental disturbances in intestinal passage to be avoided.

The exocellular proteinase or proteinases according to the invention, or the proteinase or proteinases of which the amino acid sequences have at least 60% homology with those of the exocellular proteinase or proteinases of the invention, can be used for the preparation of a medicament intended for prevention and/or treatment of diabetes, hepatic insufficiencies and disorders in intestinal passage.

5—Infectious Diseases, Immune Dysfunctions and Vaccination

It has already been indicated that PANSTIMASE® has a favourable action on GALT, and consequently on the entire immune system. Improvements in 3 different fields result.

A—Infectious Diseases

Some observations in intensive herds have shown that PANSTIMASE® often improved the state of health of the animals, which was initially attributed to the fact that it facilitated absorption of antibiotics which are added to the majority of commercial feeds. However, it was then found that this improvement was particularly significant in cases of infections by various viruses, while these are in general insensitive to the action of antibiotics. These findings relate to influenza and AUJESKY's disease in pigs, GUMBORO's disease in chickens and ecthyma in goats.

In this last case, the viral infection found in the course of a trial at an experimental station was the subject of close studies on 120 goats in total; the percentage of animals not affected was 34% for the control group and 70% for the treated group; the percentage of animals severely affected was 28% for the control group, while no animal was severely affected in the treated group.

This antiviral action can be explained by the fact that PANSTIMASE® increases the number and density of PEYER's patches, which are aggregates of immune cells distributed throughout the intestine.

B—Immune Dysfunctions

Other observations on piglets in an intensive herd have shown that PANSTIMASE® reduced the duration of the arthritis which is the inflammatory reaction consecutive to injuries to joints affecting animals reared on metal gratings. After cicatrization of the injuries, these inflammatory reactions may become progressively subdued under the action of so-called suppressive immune cells, which are numerous in the intestine and which can migrate to the inflammation zones. It is possible that PANSTIMASE® stimulates the multiplication of these cells in the intestine, and that it facilitates their migration, which would explain the fact that it reduces the duration of arthritis by about 50%.

C—Vaccinations

The improvements in the state of health found in an intensive herd can be explained by a better response to vaccinations by animals receiving a food supplemented in PANSTIMASE®. Preliminary tests in the laboratory on mice have effectively confirmed that PANSTIMASE® can increase the efficacy of vaccinations, in particular if they are carried out by the oral route.

The exocellular proteinase or proteinases according to the invention, or the proteinase or proteinases of which the amino acid sequences have at least 60% homology with those of the exocellular proteinase or proteinases of the invention, can be used for the preparation of a medicament intended for prevention and/or treatment of infectious diseases and immune dysfunctions, and for increasing the efficacy of vaccinations.

6—Hormone Insufficiencies and Degenerative Disease Associated with Ageing

It has been found that in elderly reproductive pigs, PANSTIMASE® causes a reduction in the weaning-fecundating lining interval (which tends to increase in sows) and a stimulation of sexual ardour (which tends to decline in boars). It thus seems that PANSTIMASE® enables hormone insufficiencies, and probably other adverse effects due to ageing, to be remedied.

It has effectively been found that PANSTIMASE® causes a "rejuvenation" in elderly reproductive female rats, and a reduction in the adverse affects of ageing in elderly reproductive sows and hens.

A. The first lining of the female rat is usually achieved at about the age of 70 days; when it is effected at about 140 days, the reproduction performances are poor for the control group and are better for the treated group (receiving the same food supplemented with 300 mg/kg PANSTIMASE® having a titre of 400 A.U./mg).

|  | Control group lining at 70 d | Control group lining at 140 d | Treated group lining at 140 d |
| --- | --- | --- | --- |
| Level of fecundation | 62% | 29% | 45% |
| Perinatal mortality of the rats | 18% | 35% | 18% |
| Number of rats weaned per litter | 9 | 6.6 | 8.1 |

It is found that control female rats lined at 140 d give poor results, but that treated female rats also lined at 140 d give results which approach the normal results given by control female rats lined at 70 d, and even become identical in the case of the level of perinatal mortality. It can thus be said that PANSTIMASE® caused a "rejuvenation" in female rats aged 140 d.

B. Reproductive sows are retired when they seem in a "poor condition", for example if the breeder considers that they can no longer stand up steadily nor lie down gently (instead of falling heavily, risking crushing new-born piglets). In a herd of 80 sows, before use of PANSTIMASE® the sows were retired after on average 4.4 reproduction cycles; six months after this use, it was found that the sows could be retired after on average 5.8 reproduction cycles. It can thus be considered that PANSTIMASE® enabled the productive life of sows to be prolonged, by about 30%, without an unacceptable change in their "good condition" and their performances.

During ageing, laying hens have the tendency to produce eggs which have a more fragile shell so that the percentage of cracked eggs can become greater than 10% at the end of laying. PANSTIMASE® has enabled this percentage to be reduced by half, which implies stimulation of phosphocalcium metabolism.

The exocellular proteinase or proteinases according to the invention, or the proteinase or proteinases of which the amino acid sequences have at least 60% homology with those of the exocellular proteinase or proteinases of the invention, can be used for the preparation of a medicament intended for prevention and/or treatment of hormone insufficiencies and degenerative diseases associated with ageing, for example arthritis, arthrosis and osteoporosis.

PRELIMINARY EVALUATION OF THE TOLERANCE OF PHARMACEUTICAL COMPOSITIONS ACCORDING TO THE INVENTION

Toxicological studies have shown that PANSTIMASE® has no toxicity to piglets when administered for 1 month at a dose 20 times higher than the use dose currently recommended, which is 40,000 A.U. per kg food, and no toxicity to the rat when administered for 3 months at a dose 200 times greater than this use dose.

Consequently, it has been possible to conduct a preliminary tolerance trial in man with a use dose which is relatively high with respect to the dose currently envisaged; in fact, gelatine capsules comprising 750,000 A.U. purified PANSTIMASE® (i.e. 50 mg of a batch having a titre of 15,000 A.U./mg) have been used, these being administered to patients in an amount of 2 to 3 capsules per day for 2 or 3 weeks.

24 patients (12 men—12 women) of average age 44 years, with extremes ranging from 25 to 70 years, were selected; 17 of these patients were suffering from dyspepsia in the broadest sense of the term without any organic lesion having being detectable by paraclinical investigations (laboratory tests, X-rays, in some cases endoscopy); 7 of these patients had organic lesions: 3 pancreatic, 2 gastrectomy (one for ulcer, the other for neoplasm), 2 colectomy (one for ulcero-haemorrhagic rectocolitis, the other for neoplasm). The course of the symptomatology and of the weight, if weight insufficiency, with or without wasting, existed at the start of treatment, was studied on all these 24 patients. Several subjects reported an improvement relating to regularization of intestinal passage in cases of constipation or, on the other hand, diarrhoea, and an increase in weight in cases of wasting.

A preliminary trial has also been conducted regarding cystic fibrosis in a patient aged 18 years who received 2 gelatine capsules each comprising 10,000 A.U. PANSTIMASE® every day for 3 weeks; an improvement in the symptoms was found in the intestinal region (faeces less abundant and less sticky) and in the bronchial region (expectoration easier and less frequent).

In conclusion, it can said that PANSTIMASE® was tolerated well, and that it seems to be particularly effective in cases of wasting.

The exocellular proteinase or proteinases according to the invention, or the proteinase or proteinases of which the amino acid sequences have at least 60% homology with those of the exocellular proteinase or proteinases of the invention, can be used for the preparation of a dietary composition for the nutrition of fragile or wasted subjects.

What is claimed is:

1. A method of treatment of hyperviscosity of the intestinal, bronchial and/or genital mucus in warm-blooded animals which comprises administering to warm-blood animals suffering from intestinal, bronchial and/or genital hyperviscosity of the mucus, a safe but effective amount of the proteinase composition comprising as the active ingredient the preponderant exocellular proteinase produced by a culture of Streptomyces fradiae, which is defined as having a specific activity of greater than 100,000 A.U./mg, a molecular weight around 19 kDa and an isoelectric point around 8.5 and which is capable of selectively destroying sub-unit A of cholera toxin, without destroying sub-unit B of cholera toxin, admixed or combined with an inert-non-toxic physiologically acceptable diluent or vehicle.

2. The method of claim 1, wherein the proteinase composition further comprises at least one of the two exocellular proteinases produced by Streptomyces fradiae.

3. A method of improving the absorption of drugs administered to warm-blooded animals in need thereof comprising simultaneously administering to a patient suffering from said malabsorption, a safe but effective amount of a proteinase composition comprising as the active ingredient the preponderant exocellular proteinase produced by a culture of Streptomyces fradiae, which is defined as having a specific activity greater than 100,000 A.U./mg, a molecular weight around 19 kDa and an isoelectric point around 8.5 and which is capable of selectively destroying sub-unit A of cholera toxin, without destroying the sub-unit B, admixed or combined with an inert-non-toxic physiologically acceptable diluent or vehicle.

4. A method for treating prolonged adhesion of infectious germs to the mucosae, for improving regeneration of atrophied or destroyed villi of the intestinal mucosae, and for treating digestive ulcers and enterotoxaemias in warm-blooded animals, comprising administering to patients suffering from said illnesses, a safe but effective amount of a proteinase composition comprising as the active ingredient the preponderant exocellular proteinase produced by a culture of Streptomyces fradiae, which is defined as having a specific activity greater than 100,000 A.U./mg, a molecular weight around 19 kDa and an isoelectric point around 8.5 and which is capable of selectively destroying sub-unit A of cholera toxin, without destroying the sub-unit B, admixed or combined with an inert-non-toxic physiologically acceptable diluent or vehicle.

5. A method for treating diabetes or hepatic insufficiencies and/or disorders in the intestinal passage in warm-blooded animals, comprising administering to patients suffering from diabetes and/or hepatic insufficiencies and/or disorders of the intestinal passage, a safe but effective amount of a proteinase composition comprising as the active ingredient the preponderant exocellular proteinase produced by a culture of *Streptomyces fradiae*, which is defined as having a specific activity greater than 100,000 A.U./mg a molecular weight around 19 kDa and an isoelectric point around 8.5 and which is capable of selectively destroying sub-unit A of cholera toxin, without destroying the sub-unit B, admixed or combined with an inert-non-toxic physiologically acceptable diluent or vehicle.

6. A method of treating infectious diseases and immune dysfunctions, comprising administering to patients suffering from infectious diseases and immune dysfunctions, a same but effective amount of a proteinase composition comprising as the active ingredient the preponderant exocellular proteinase produced by a culture of *Streptomyces fradiae*, which is defined as having a specific activity greater than 100,000 A.U./mg a molecular weight around 19 kDa and an isoelectric point around 8.5 and which is capable of selectively destroying sub-unit A of cholera toxin, without destroying the sub-unit B, admixed or combined with an inert-non-toxic physiologically acceptable diluent or vehicle.

7. A method for improving the efficiency of vaccinations in warm-blooded animals suffering from lack of efficiency or vaccinations, comprising administering to said patients a safe but effective amount of a composition comprising as the active ingredient the preponderant exocellular proteinase produced by a culture of *Streptomyces fradiae*, which is defined as having a specific activity greater than 100,000 A.U./mg a molecular weight around 19 kDa and an isoelectric point around 8.5 and which is capable of selectively destroying sub-unit A of cholera toxin, without destroying the sub-unit B, admixed or combined with an inert-non-toxic physiologically acceptable diluent or vehicle.

8. A method for treating hormone insufficiencies and degenerative diseases connected to ageing in warm-blooded animals, comprising administering to patients suffering from hormone insufficiencies and degenerative diseases connected to ageing, a safe but effective amount of a proteinase composition of comprising as the active ingredient the preponderant exocellular proteinase produced by a culture of *Streptomyces fradiae*, which is defined as having a specific activity greater than 100,000 A.U./mg a molecular weight around 19 kDa and an isoelectric point around 8.5 and which is capable of selectively destroying sub-unit A of cholera toxin, without destroying the sub-unit B, admixed or combined with an inert-non-toxic physiologically acceptable diluent or vehicle.

9. A method for improving the nutrition of fragile or wasted subjects, comprising administering to said subjects a dietary composition alleviating such disorders comprising as the active ingredient the preponderant exocellular proteinase produced by a culture of *Streptomyces fradiae*, having a specific activity greater than 100,000 A.U./mg, a molecular weight about 19 kDa, and an isolectric point about 8.5 and which is capable of selectively destroying the sub-unit A of cholera toxin without destroying the sub-unit B as a mixture or in a combination with an inert, nontoxic physiologically acceptable diluent.

* * * * *